US012653664B2

(12) United States Patent
Li et al.

(10) Patent No.: US 12,653,664 B2
(45) Date of Patent: Jun. 16, 2026

(54) INTRAOCULAR LENS (IOL) BASED ON METASURFACE

(71) Applicant: Wenzhou Institute, University of Chinese Academy Of Sciences, Wenzhou (CN)

(72) Inventors: Tao Li, Wenzhou (CN); Binbin Yu, Wenzhou (CN)

(73) Assignee: Wenzhou Institute, University of Chinese Academy Of Sciences, Wenzhou (CN)

( * ) Notice: Subject to any disclaimer, the term of this patent is extended or adjusted under 35 U.S.C. 154(b) by 888 days.

(21) Appl. No.: 17/913,068

(22) PCT Filed: Jun. 28, 2022

(86) PCT No.: PCT/CN2022/101735
§ 371 (c)(1),
(2) Date: Sep. 20, 2022

(87) PCT Pub. No.: WO2023/274186
PCT Pub. Date: Jan. 5, 2023

(65) Prior Publication Data
US 2023/0397983 A1 Dec. 14, 2023

(30) Foreign Application Priority Data

Jun. 28, 2021 (CN) .......................... 202110719765.0

(51) Int. Cl.
A61F 2/16 (2006.01)
(52) U.S. Cl.
CPC ............ A61F 2/164 (2015.04); A61F 2/1627 (2013.01); A61F 2/1629 (2013.01); A61F 2/1648 (2013.01)

(58) Field of Classification Search
CPC ...... A61F 2/164; A61F 2/1627; A61F 2/1629; A61F 2/1648
See application file for complete search history.

(56) References Cited

U.S. PATENT DOCUMENTS

2010/0321635 A1* 12/2010 Apter .................... G02C 7/042
351/159.75
2014/0277432 A1* 9/2014 Silvestrini ............. G02F 1/0126
623/6.17

(Continued)

*Primary Examiner* — Jerrah Edwards
*Assistant Examiner* — Aren Patel
(74) *Attorney, Agent, or Firm* — Lerner David LLP

(57) ABSTRACT

An intraocular lens (IOL) based on a metasurface, includes: a front optical lens, a rear optical lens, an equatorial plane, and an optical loop. The front optical lens and the rear optical lens are connected through the equatorial plane. The optical loop is connected with the equatorial plane. A metasurface structure is arranged on the equatorial plane. The metasurface structure includes a plurality of nanostructure units with a phase distribution of a planar axicon lens. A Gaussian beam is generated based on a biconvex lens structure of a conventional IOL, and the phase distribution of the planar axicon lens is loaded through a geometric phase of the metasurface structure, such that a Bessel-Gaussian beam is generated. When the beam is propagated in a free space, a cross section of the beam is not changed along with a propagation distance, such that the Bessel-Gaussian beam keeps a relatively consistent focal plane within a certain propagation distance, thereby realizing characteristics of long focal depth, adjustable refraction, and achromatism.

7 Claims, 2 Drawing Sheets

(56) References Cited

U.S. PATENT DOCUMENTS

| | | | |
|---|---|---|---|
| 2021/0033887 A1* | 2/2021 | Newman | B29D 11/0048 |
| 2021/0275294 A1* | 9/2021 | Zhang | A61B 1/00174 |
| 2022/0252849 A1* | 8/2022 | Lee | A61F 2/1648 |
| 2023/0101527 A1* | 3/2023 | Bakaraju | G02B 3/02 |
| | | | 351/159.42 |

* cited by examiner

INTRAOCULAR LENS (IOL) BASED ON METASURFACE

CROSS REFERENCE TO RELATED APPLICATION

The present application is a national phase entry under 35 U.S.C.§ 371 of International Application No. PCT/CN2022/101735, filed Jun. 28, 2022, which claims the priority of Chinese Patent Application No. 202110719765.0, entitled "INTRAOCULAR LENS (IOL) BASED ON METASUR-FACE" and filed with China National Intellectual Property Administration (CNIPA) on Jun. 28, 2021, which is incorporated by reference herein in its entirety.

TECHNICAL FIELD

The present disclosure relates to the field of ophthalmic medical equipment, and in particular, to an IOL based on a metasurface.

BACKGROUND ART

The visual system is an important part of human life. Its principle of visual imaging is that a reflected object is transmitted to the lens with variable shape and adjustable position through a pupil in the form of light, mapped to the central retina after transmission and inverted imaging, and received by the optic nerve to form visual images. The refractive adjustment of the lens is controlled by the ciliary muscle, and the clarity of retinal imaging is controlled by the transparency of the lens. The lens is composed of protein, etc. With the increase of human age or other external factors, it is easy to cause the deformation and turbidity of the protein, which reduces the light transmittance of the original highly transparent lens and reduces the refractive power to cause cataracts even blindness.

For cataracts that significantly affect vision, the most common treatment currently is cataract surgery for removing the deformed and turbid lens through phacoemulsification and implanting an IOL as a substitute. The IOL replaces the natural ocular lens in an anatomical position, and thus patients can got a vision level close to a normal vision level through the implementation of implantation. However, the IOL that has been put into clinical application still have problems such as insufficient postoperative adjustment power and decreased adjustment function with time, and the IOL does not have universal applicability, cannot eliminate chromatic aberration excellently, and does not have a long focal depth. Based on the problems and difficulties in clinical application, it is urgently necessary how to develop an IOL with life characteristics, which can not only meet the basic functions of current products, but also realize the characteristics of adjustable refraction, achromatism, and long focal depth.

SUMMARY

An objective of the present disclosure is to provide an IOL based on a metasurface to realize functions of long focal depth, adjustable refraction, and achromatism.

To achieve the above objectives, the present disclosure provides an IOL based on a metasurface, including:

a front optical lens, a rear optical lens, an equatorial plane, and an optical loop; where the front optical lens and the rear optical lens are connected through the equatorial plane, the optical loop is connected with the equatorial plane, and a metasurface structure is arranged on the equatorial plane, and where the metasurface structure includes a plurality of nanostructure units with a phase distribution of a planar axicon lens.

Optionally, each of the plurality of nanostructure units in the metasurface structure may be distributed according to $\varphi_{axicon}=2*\alpha$, where $\alpha$ is a rotation angle of the nanostructure unit, $\varphi_{axicon}$ is the phase distribution of the planar axicon lens, and $*$ is a multiplication sign.

Optionally, a phase distribution formula of the planar axicon lens may be:

$$\begin{cases} \varphi_{axicon} = \sqrt{x^2 + y^2} * 2\pi/\lambda * \sin\beta \\ \qquad \beta = \tan^{-1}(R/f) \end{cases},$$

where $\varphi_{axicon}$ is the phase distribution of the planar axicon lens, x and y are position coordinates of a two-dimensional coordinate system with a center of the planar axicon lens as an origin respectively, $\lambda$ is an incident wavelength, f is a focal length corresponding to a maximum aperture R of the metasurface structure and is a focal length under static refractive power +58.64D, and $\beta$ is a maximum angle corresponding to the metasurface structure.

Optionally, structural dimensions of the plurality of nanostructure units may be determined by an incident wavelength.

Optionally, when the incident wavelength $\lambda=600$ nm, each nanostructure unit may have a height H of 300 nm, a width W of 110 nm, a length L of 310 nm, and a lattice constant d of 470 nm.

Optionally, the metasurface structure may include 212, 345,780 nanostructure units and be arranged with a total of 2,660 rings.

Optionally, the plurality of nanostructure units may be made of polymethyl methacrylate (PMMA).

Optionally, a refractive index of each nanostructure unit may be in a visible light range of [1.46, 1.49].

Optionally, a thickness of the metasurface structure may be 300 nm.

According to the specific embodiments provided by the present disclosure, the present disclosure discloses the following technical effects:

The present disclosure provides the IOL based on a metasurface, which takes three-dimensional surface contour parameters presented by the human eye lens under the standard eye static refraction power +58.64D as a design standard of the three-dimensional surface contour model of the IOL, and designs the metasurface structure for the metasurface on the equatorial plane of the IOL. A Gaussian beam is generated based on a biconvex lens structure of a conventional IOL, and the phase distribution of the planar axicon lens is loaded through a geometric phase of the metasurface structure, such that a Bessel-Gaussian beam is generated. When the beam propagates in a free space, a cross section of the beam is not changed along with a propagation distance, such that the Bessel-Gaussian beam keeps a relatively consistent focal plane within a certain propagation distance, thereby realizing characteristics of long focal depth, adjustable refraction, and achromatism.

BRIEF DESCRIPTION OF THE DRAWINGS

To describe the embodiments of the present disclosure or the technical solutions in the prior art more clearly, the accompanying drawings required in the embodiments are briefly introduced below. Obviously, the accompanying drawings described below are only some embodiments of the present disclosure. Those of ordinary skill in the art may further obtain other accompanying drawings based on these accompanying drawings without creative effort.

REFERENCE NUMERALS

1, equatorial plane, 2, metasurface structure, 3, optical loop, 4, front optical lens, and 5, rear optical lens.

DETAILED DESCRIPTION OF THE EMBODIMENTS

The technical solutions of the embodiments of the present disclosure are clearly and completely described below with reference to the accompanying drawings. Apparently, the described embodiments are merely a part rather than all of the embodiments of the present disclosure. All other embodiments obtained by those of ordinary skill in the art based on the embodiments of the present disclosure without creative efforts shall fall within the protection scope of the present disclosure.

An objective of the present disclosure is to provide an IOL based on a metasurface to realize functions of long focal depth, adjustable refraction, and achromatism.

To make the above-mentioned objective, features, and advantages of the present disclosure clearer and more comprehensible, the present disclosure will be further described in detail below in conjunction with the accompanying drawings and specific embodiments.

In recent years, the progress of nanotechnology has enabled a manipulation of materials at an atomic level, which is helpful to the development of new optical materials. In 1999, a concept of metamaterial was proposed by Professor Rodger M. Walser from the University of Texas. The metamaterial is a three-dimensional artificial composite material constructed by subwavelength artificial microstructures (artificial atoms) with specific electromagnetic properties in a certain arrangement, showing a strong ability to control electromagnetic waves, and realizing physical phenomena and functions that cannot be achieved by natural materials. Through structural adjustment, the metamaterial can in principle be designed with any permittivity and magnetic conductivity, thus producing many wave manipulation effects that cannot be achieved by natural materials. But as a 3D structure, metamaterials are designed to be still overly complicated, and optical materials should be thinner and more efficient. Thus, a concept of metasurface came into being. In short, the metasurfaces can be viewed as a 2D version of metamaterials, which is constructed by planar subatoms. These atoms purposely select electromagnetic responses in a specific order and use abrupt phase transitions on the surface of the structure to transmit or reflect waves. Therefore, the present disclosure adopts the most advanced metasurface technology in the current optical field to construct a novel IOL with functions of long focal depth and achromatism under stepless zoom.

Figures 1, 2:
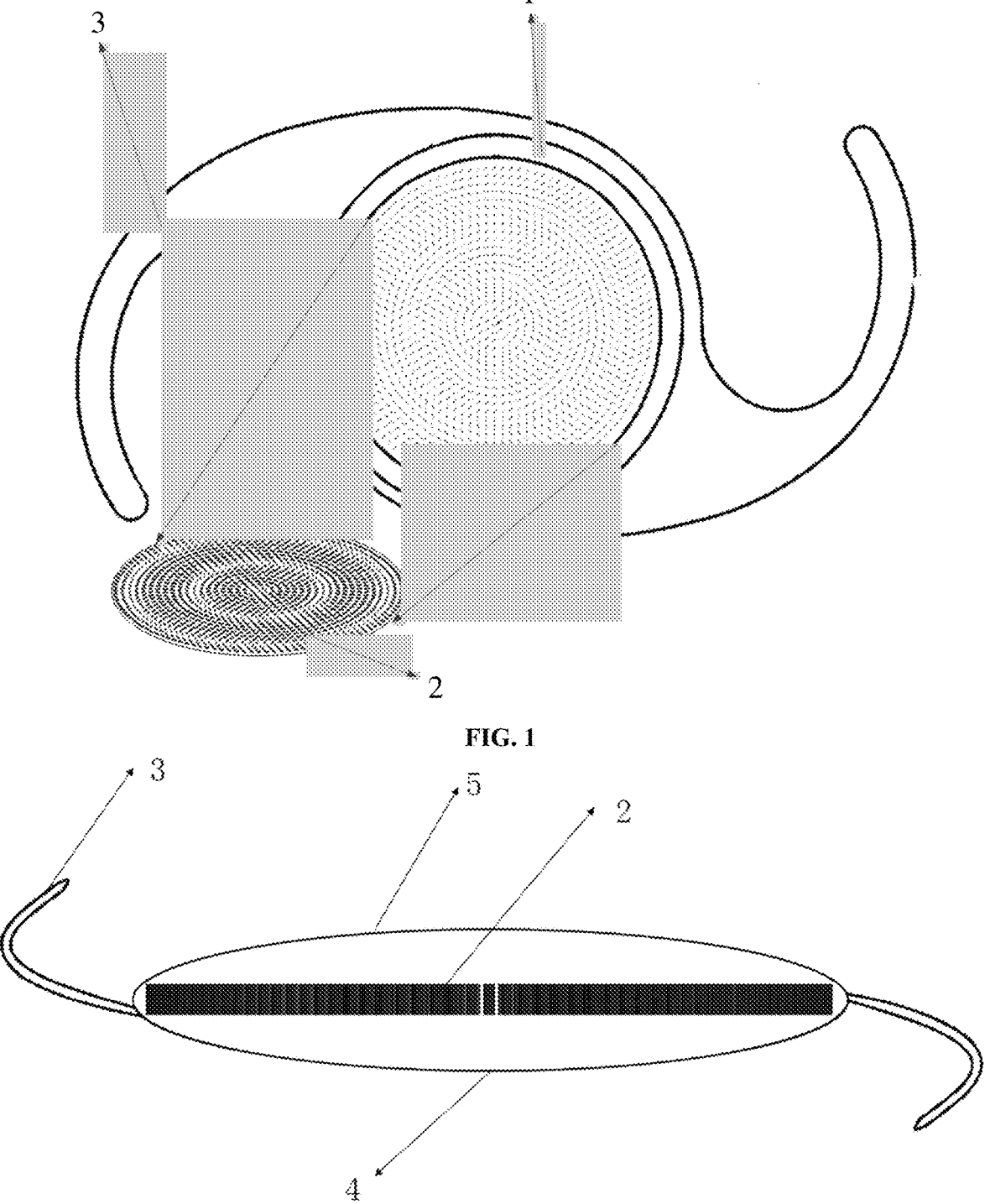
FIG. 1 is a front view of a structure of an IOL based on a metasurface of the present disclosure.
FIG. 2 is a side view of a structure of the IOL based on a metasurface of the present disclosure.

As shown in FIG. 1 to FIG. 2, the present disclosure provides an IOL based on a metasurface, including: a front optical lens 4, a rear optical lens 5, an equatorial plane 1, and an optical loop 3. The front optical lens 4 and the rear optical lens 5 are connected through the equatorial plane 1. The optical loop 3 is connected with the equatorial plane 1. A metasurface structure 2 is arranged on the equatorial plane 1. The metasurface structure 2 includes a plurality of nanostructure units with a phase distribution of a planar axicon lens. In the present disclosure, the phase distributions of the planar axicon lens at different positions are attached to the nanostructure units of the metasurface structure through the design of the metasurface structure 2, such that a Bessel-Gaussian beam is generated. When the Bessel-Gaussian beam propagates in a free space, a cross section of the beam is not changed along with the propagation distance, such that the Bessel-Gaussian beam keeps a relatively consistent focal plane within a certain propagation distance, thereby realizing characteristics of long focal depth, adjustable refraction, and achromatism.

In an optional embodiment, each of the plurality of nanostructure units in the metasurface structure 2 of the present disclosure is distributed according to $\varphi_{axicon}=2*\alpha$, where $\alpha$ is a rotation angle of the nanostructure unit, $\varphi_{axicon}$ is the phase distribution of the planar axicon lens, and * is a multiplication sign. In the present embodiment, a phase distribution formula of the planar axicon lens is:

$$\begin{cases} \varphi_{axicon} = \sqrt{x^2 + y^2} * 2\pi/\lambda * \sin\beta \\ \beta = \tan^{-1}(R/f) \end{cases},$$

where $\varphi_{axicon}$ is the phase distribution of the planar axicon lens, x and y are position coordinates of a two-dimensional coordinate system with a center of the planar axicon lens as an origin respectively, $\lambda$ is an incident wavelength, f is a focal length corresponding to a maximum aperture R of the metasurface structure and is a focal length under static refractive power +58.64D, that is, f=17.053 mm, and $\beta$ is a maximum angle corresponding to the metasurface structure, that is, R=2.5 mm, and $\beta=\tan^-(2.5/17.053)=8.34°$.

Figure 3:
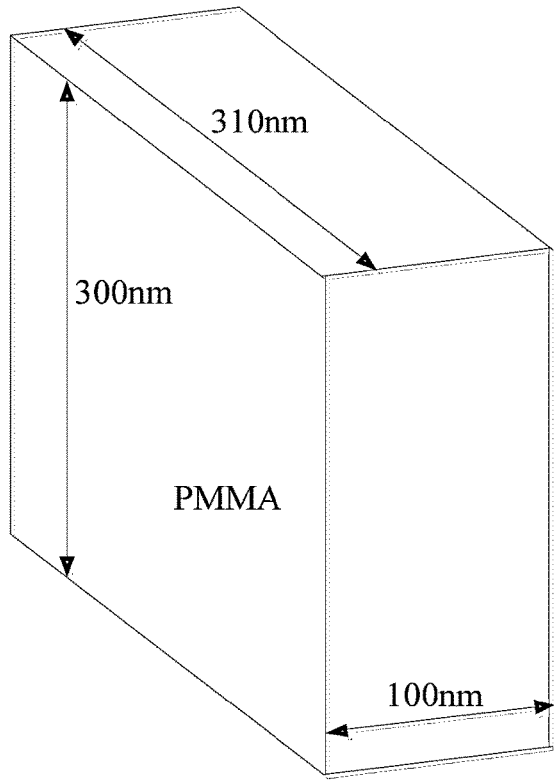
FIG. 3 is a schematic diagram of a nanostructure unit in a metasurface structure of the present disclosure.

In an optional embodiment, structural dimensions of the plurality of nanostructure units of the present disclosure are determined by an incident wavelength. In the present embodiment, taking the incident wavelength $\lambda$=600 nm as an example, each nanostructure unit has a height H of 300 nm, a width W of 110 nm, a length L of 310 nm, and a lattice constant d of 470 nm, as shown in FIG. 3.

In an optional embodiment, the plurality of nanostructure units of the present disclosure are made of PMMA. The nanostructure unit has a refractive index in a visible light range of [1.46, 1.49].

On an equatorial plane of a conventional IOL, the nanostructure units of a metasurface structure are constructed by techniques such as photolithography or nanoimprinting, and are orderly arranged according to a formula between the phase and the rotation angle of the nanostructure unit (i.e. $\varphi_{axicon}=2*\alpha$). In the present embodiment, the metasurface structure 2 is arranged with a total of 2,660 rings, and designed with 212,345,780 nanostructure units. The frontal schematic distribution diagram of the metasurface structure 2 is shown in FIG. 1. Since the feature size of the metasurface structure 2 is too small, feature structure details of the metasurface structure 2 cannot be reasonably displayed when compared with macroscopic objects such as the IOLs. Therefore, the designed metasurface structure is partially magnified by 133 times.

In the present embodiment, as shown in FIG. 2, the front and rear of the equatorial plane 1 are optical lens surfaces of aspherical surfaces of conventional IOLs, and a layer of metasurface structure 2 with a thickness of 300 nm is provided on the equatorial plane.

Figure 4:
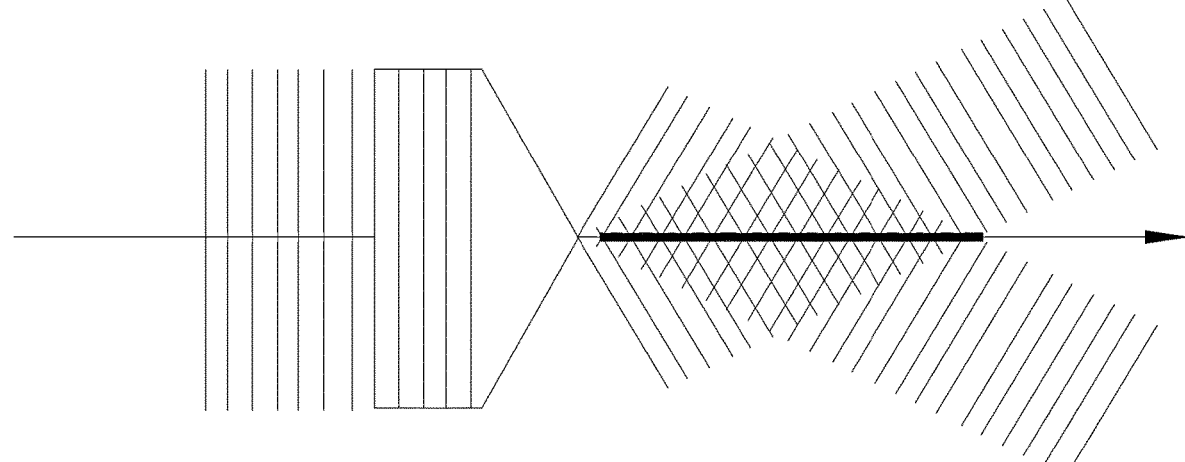
FIG. 4 is an optical path diagram of a Bessel beam generated by an axicon lens in the present disclosure.

The IOL based on a metasurface provided by the present disclosure takes three-dimensional surface contour parameters presented by the human eye lens under the standard eye static refraction power +58.64D as a design standard of the three-dimensional surface contour model of the IOL. On this basis, the metasurface is designed on the equatorial plane of the IOL. Different from the fact that a Gaussian beam is generated based on a biconvex lens structure of the conventional IOL, the phase distribution of the planar axicon lens is loaded through a geometric phase of the metasurface structure, such that a Bessel-Gaussian beam is generated. A cross section of the beam is not changed along with a propagation distance, such that the Bessel-Gaussian beam keeps a relatively consistent focal plane within a certain propagation distance, thereby realizing characteristics of a long focal depth, adjustable refraction, and achromatism, as shown in FIG. 4.

Various embodiments of the present specification are described in a progressive manner, each embodiment focuses on differences from other embodiments, and the same and similar parts between the various embodiments may be referred to each other.

In this specification, some specific examples are used for illustration of the principles and implementations of the present disclosure. The description of the foregoing embodiments is used to help illustrate the method of the present disclosure and the core ideas thereof. In addition, those of ordinary skill in the art can make various modifications in terms of specific implementations and the scope of application in accordance with the ideas of the present disclosure. In conclusion, the content of the present description shall not be construed as limitations to the present disclosure.

What is claimed is:

1. An intraocular lens (IOL) based on a metasurface, comprising:

a front optical lens, a rear optical lens, an equatorial plane, and an optical loop, wherein the front optical lens and the rear optical lens are connected through the equatorial plane, the optical loop is connected with the equatorial plane, and a metasurface structure is arranged on the equatorial plane; and the metasurface structure comprises a plurality of nanostructure units with a phase distribution of a planar axicon lens; the each of the plurality of nanostructure units, $\varphi_{axicon}$ is the phase distribution of the planar axicon lens, and * is a multiplication sign; and the phase distribution formula of the planar axicon lens is:

$$\begin{cases} \varphi_{axicon} = \sqrt{x^2 + y^2} * 2\pi/\lambda * \sin\beta, \\ \beta = \tan^{-1}(R/f) \end{cases},$$

wherein $\varphi_{axicon}$ is the phase distribution of the planar axicon lens, x and y are position coordinates of a two-dimensional coordinate system with a center of the planar axicon lens as an origin respectively, $\lambda$ is an incident wavelength, f is a focal length corresponding to a maximum aperture R of the metasurface structure and is a focal length under static refractive power +58.64D, and $\beta$ is a maximum angle corresponding to the metasurface structure.

2. The IOL based on the metasurface according to claim 1, wherein structural dimensions of the plurality of nanostructure units are determined by an incident wavelength.

3. The IOL based on the metasurface according to claim 2, wherein when the incident wavelength $\lambda$ is 600 nm, the each of the plurality of nanostructure units has a height H of 300 nm, a width W of 110 nm, a length L of 310 nm, and a lattice constant d of 470 nm.

4. The IOL based on the metasurface according to claim 1, wherein the metasurface structure comprises 212,345,780 nanostructure units and is arranged with a total of 2,660 rings.

5. The IOL based on the metasurface according to claim 4, wherein the each of the plurality of nanostructure units is made of polymethyl methacrylate (PMMA).

6. The IOL based on the metasurface according to claim 1, wherein a refractive index of the each of the plurality of nanostructure units is in a visible light range of [1.46, 1.49].

7. The IOL based on the metasurface according to claim 1, wherein a thickness of the metasurface structure is 300 nm.

* * * * *